US009631615B2

(12) United States Patent
Miyazaki et al.

(10) Patent No.: US 9,631,615 B2
(45) Date of Patent: *Apr. 25, 2017

(54) CONTROL UNIT, TUBE UNIT, AND MICROPUMP

(71) Applicant: Seiko Epson Corporation, Tokyo (JP)

(72) Inventors: Hajime Miyazaki, Matsumoto (JP); Kazuo Kawasumi, Chino (JP)

(73) Assignee: Seiko Epson Corporation (JP)

( * ) Notice: Subject to any disclaimer, the term of this patent is extended or adjusted under 35 U.S.C. 154(b) by 349 days.

This patent is subject to a terminal disclaimer.

(21) Appl. No.: 13/929,103

(22) Filed: Jun. 27, 2013

(65) Prior Publication Data

US 2013/0287606 A1 Oct. 31, 2013

Related U.S. Application Data

(62) Division of application No. 12/542,751, filed on Aug. 18, 2009, now Pat. No. 8,491,284.

(30) Foreign Application Priority Data

Sep. 29, 2008 (JP) ................................. 2008-249798

(51) Int. Cl.
  *F04B 43/08* (2006.01)
  *F04B 43/09* (2006.01)
  (Continued)

(52) U.S. Cl.
  CPC .......... *F04B 43/09* (2013.01); *A61M 5/14228* (2013.01); *F04B 43/082* (2013.01); *F04B 43/1223* (2013.01); *A61M 2205/12* (2013.01)

(58) Field of Classification Search
  CPC .... F04B 43/082; F04B 43/09; F04B 43/1223; A61M 5/14228; A61M 2205/12
  See application file for complete search history.

(56) References Cited

U.S. PATENT DOCUMENTS

| 3,447,478 A | * | 6/1969 | Clemens | ............. F04B 43/1253 417/477.8 |
| 3,574,883 A | | 4/1971 | Brittain et al. | |

(Continued)

FOREIGN PATENT DOCUMENTS

| EP | 0 570 134 A2 | 11/1993 |
| JP | 54-103290 | 8/1979 |

(Continued)

OTHER PUBLICATIONS

Communication from the European Patent Office dated Nov. 19, 2010, Application No. 09171345.3.

(Continued)

*Primary Examiner* — Devon Kramer
*Assistant Examiner* — Joseph Herrmann
(74) *Attorney, Agent, or Firm* — Harness, Dickey & Pierce, P.L.C.

(57) ABSTRACT

A micropump including a tube unit including an elastic tube disposed in an arc shape, a plurality of fingers disposed radially from the arc shape of the tube, and a guide frame, which holds the tube and the plurality of fingers. The micropump also includes a control unit including a cam that presses the plurality of fingers, a drive section that applies torque to the cam, a control circuit that carries out a drive control of the drive section, and a machine casing that holds the cam, drive section, and control circuit. The tube unit is mountable in and removable from the control unit in a direction approximately parallel to the plane of rotation of the cam, and is mounted inside a space provided in the machine casing.

10 Claims, 10 Drawing Sheets

(51) Int. Cl.
*A61M 5/142* (2006.01)
*F04B 43/12* (2006.01)

(56) References Cited

U.S. PATENT DOCUMENTS

| | | | |
|---|---|---|---|
| 3,630,647 A | 12/1971 | Kochlin | |
| 3,990,444 A | 11/1976 | Vial | |
| 4,155,362 A | 5/1979 | Jess | |
| 4,187,057 A | 2/1980 | Xanthopoulos | |
| 4,327,780 A | 5/1982 | Lehmann | |
| 4,479,797 A | 10/1984 | Kobayashi et al. | |
| 4,607,764 A | 8/1986 | Christine | |
| 4,648,812 A | 3/1987 | Kobayashi et al. | |
| 4,735,558 A | 4/1988 | Kienholz et al. | |
| 4,869,646 A | 9/1989 | Gordon et al. | |
| 4,909,710 A | 3/1990 | Kaplan et al. | |
| 4,954,046 A | 9/1990 | Irvin et al. | |
| 5,049,047 A | 9/1991 | Polaschegg et al. | |
| 5,083,908 A | 1/1992 | Gagnebin et al. | |
| 5,094,820 A | 3/1992 | Maxwell et al. | |
| 5,249,937 A | 10/1993 | Aubert | |
| 5,308,335 A * | 5/1994 | Ross | A61M 5/14244 604/141 |
| 5,318,413 A | 6/1994 | Bertoncini | |
| 5,320,502 A | 6/1994 | Davis | |
| 5,342,180 A | 8/1994 | Daoud | |
| 5,472,368 A | 12/1995 | Zollig | |
| 5,511,951 A | 4/1996 | O'Leary | |
| 5,513,957 A | 5/1996 | O'Leary | |
| 5,531,697 A | 7/1996 | Olsen et al. | |
| 5,531,698 A | 7/1996 | Olsen | |
| 5,575,631 A | 11/1996 | Jester | |
| 5,647,854 A | 7/1997 | Olsen et al. | |
| 5,658,252 A | 8/1997 | Johnson | |
| 5,683,233 A * | 11/1997 | Moubayed | A61M 5/14228 417/474 |
| 5,791,881 A | 8/1998 | Moubayed et al. | |
| 5,817,116 A | 10/1998 | Takahashi et al. | |
| 5,924,852 A | 7/1999 | Moubayed et al. | |
| 5,980,490 A | 11/1999 | Tsoukalis | |
| 6,030,190 A | 2/2000 | Kammerer | |
| 6,106,249 A | 8/2000 | Barak | |
| 6,123,686 A | 9/2000 | Olsen et al. | |
| 6,164,921 A * | 12/2000 | Moubayed | A61M 5/14228 251/7 |
| 6,203,296 B1 * | 3/2001 | Ray | A61M 5/142 417/477.2 |
| 6,253,968 B1 | 7/2001 | Van Dijk et al. | |
| 6,371,732 B1 | 4/2002 | Moubayed et al. | |
| 6,558,347 B1 | 5/2003 | Jhuboo et al. | |
| 6,749,587 B2 | 6/2004 | Flaherty | |
| 6,835,049 B2 | 12/2004 | Ray | |
| 6,872,058 B2 | 3/2005 | Doig | |
| 6,918,748 B2 | 7/2005 | Miyazawa | |
| 7,036,751 B1 | 5/2006 | Lund et al. | |
| 7,059,840 B2 | 6/2006 | Corwin et al. | |
| 7,078,847 B2 | 7/2006 | Miyazawa et al. | |
| 7,116,037 B2 | 10/2006 | Moteki et al. | |
| 7,238,010 B2 | 7/2007 | Hershberger et al. | |
| 7,527,608 B2 | 5/2009 | Mason | |
| 7,556,481 B2 | 7/2009 | Moubayed | |
| 7,632,079 B2 | 12/2009 | Hershberger et al. | |
| 7,762,795 B2 | 7/2010 | Moubayed | |
| 7,963,690 B2 | 6/2011 | Thompson et al. | |
| 8,137,314 B2 | 3/2012 | Mounce et al. | |
| 8,152,498 B2 | 4/2012 | Bunoz | |
| 8,246,321 B2 * | 8/2012 | Miyazaki | A61M 5/14228 417/316 |
| 8,491,286 B2 | 7/2013 | Miyazaki et al. | |
| 8,679,062 B2 | 3/2014 | Yodfat et al. | |
| 2002/0169439 A1 * | 11/2002 | Flaherty | A61M 5/14248 604/891.1 |
| 2004/0116862 A1 * | 6/2004 | Ray | A61M 5/14232 604/151 |
| 2004/0199118 A1 | 10/2004 | Christenson et al. | |
| 2004/0234401 A1 | 11/2004 | Banister | |
| 2006/0029505 A1 | 2/2006 | Gibson et al. | |
| 2006/0073048 A1 | 4/2006 | Malackowski | |
| 2006/0253086 A1 | 11/2006 | Moberg et al. | |
| 2007/0106218 A1 | 5/2007 | Yodfat et al. | |
| 2007/0128060 A1 | 6/2007 | Miyazaki et al. | |
| 2007/0154336 A1 | 7/2007 | Miyazaki et al. | |
| 2007/0217932 A1 | 9/2007 | Voyeux et al. | |
| 2007/0231205 A1 | 10/2007 | Williams et al. | |
| 2008/0051709 A1 | 2/2008 | Mounce et al. | |
| 2008/0065016 A1 | 3/2008 | Peterson et al. | |
| 2008/0101967 A1 | 5/2008 | Moubayed | |
| 2008/0101968 A1 | 5/2008 | Moubayed | |
| 2008/0138218 A1 * | 6/2008 | Miyazaki | A61M 5/14228 417/410.3 |
| 2008/0138222 A1 | 6/2008 | Miyazaki et al. | |
| 2008/0159890 A1 | 7/2008 | Miyazaki et al. | |
| 2008/0215035 A1 | 9/2008 | Yodfat et al. | |
| 2008/0255516 A1 * | 10/2008 | Yodfat | A61M 5/14248 604/151 |
| 2008/0304982 A1 | 12/2008 | Miyazaki et al. | |
| 2009/0060755 A1 | 3/2009 | Miyazaki | |
| 2009/0081078 A1 | 3/2009 | Caramuta | |
| 2009/0196776 A1 | 8/2009 | Moubayed | |
| 2009/0208350 A1 | 8/2009 | Miyazaki et al. | |
| 2009/0240201 A1 | 9/2009 | Rotem et al. | |
| 2009/0240210 A1 | 9/2009 | Walton et al. | |
| 2009/0312708 A1 | 12/2009 | Miyazaki et al. | |
| 2010/0021315 A1 | 1/2010 | Wolff | |
| 2010/0047099 A1 | 2/2010 | Miyazaki et al. | |
| 2010/0074781 A1 | 3/2010 | Miyazaki et al. | |
| 2010/0080720 A1 | 4/2010 | Miyazaki et al. | |
| 2010/0121306 A1 | 5/2010 | Yodfat et al. | |
| 2010/0137802 A1 | 6/2010 | Yodfat et al. | |
| 2010/0143168 A1 | 6/2010 | Miyazaki et al. | |
| 2010/0296955 A1 | 11/2010 | Wolff | |
| 2011/0002801 A1 | 1/2011 | Miyazaki et al. | |
| 2011/0186143 A1 | 8/2011 | Miyazaki et al. | |
| 2011/0186598 A1 | 8/2011 | Thompson et al. | |
| 2011/0186599 A1 | 8/2011 | Thompson et al. | |
| 2011/0305588 A1 | 12/2011 | Miyazaki et al. | |
| 2012/0027624 A1 | 2/2012 | Miyazaki et al. | |

FOREIGN PATENT DOCUMENTS

| | | |
|---|---|---|
| JP | 62-258178 | 11/1987 |
| JP | 63-83477 | 6/1988 |
| JP | 3177742 U | 11/1990 |
| JP | 05-168709 | 7/1993 |
| JP | 05-314607 | 11/1993 |
| JP | 06-021488 | 6/1994 |
| JP | 07-059853 A | 3/1995 |
| JP | 09-262283 | 10/1997 |
| JP | 09-291885 | 11/1997 |
| JP | 10-028731 | 2/1998 |
| JP | 10-193651 | 7/1998 |
| JP | 3177742 B2 | 6/2001 |
| JP | 2001-515557 A | 9/2001 |
| JP | 2004-082245 A | 3/2004 |
| JP | 2004-532670 A | 10/2004 |
| JP | 2005-011983 A | 1/2005 |
| JP | 2005-046632 A | 2/2005 |
| JP | 2005-168958 A | 6/2005 |
| JP | 2005-337212 A | 12/2005 |
| JP | 2005-351131 A | 12/2005 |
| JP | 2006-034845 A | 2/2006 |
| JP | 2006-242116 A | 9/2006 |
| JP | 2006-314346 A | 11/2006 |
| JP | 2007-275548 A | 10/2007 |
| JP | 2008-136525 A | 6/2008 |
| JP | 2008-161669 A | 7/2008 |
| JP | 2008-202602 A | 9/2008 |
| JP | 2008-202603 A | 9/2008 |
| WO | WO-97-34084 A1 | 9/1997 |

OTHER PUBLICATIONS

California, State of. "Batteries." Batteries. N.p., May 29, 2014.

(56) References Cited

OTHER PUBLICATIONS

Web. Jul. 21, 2016. states as of Feb. 8, 2006 all batteries are considered hazardous waste and must be recycled in the state of California.

* cited by examiner

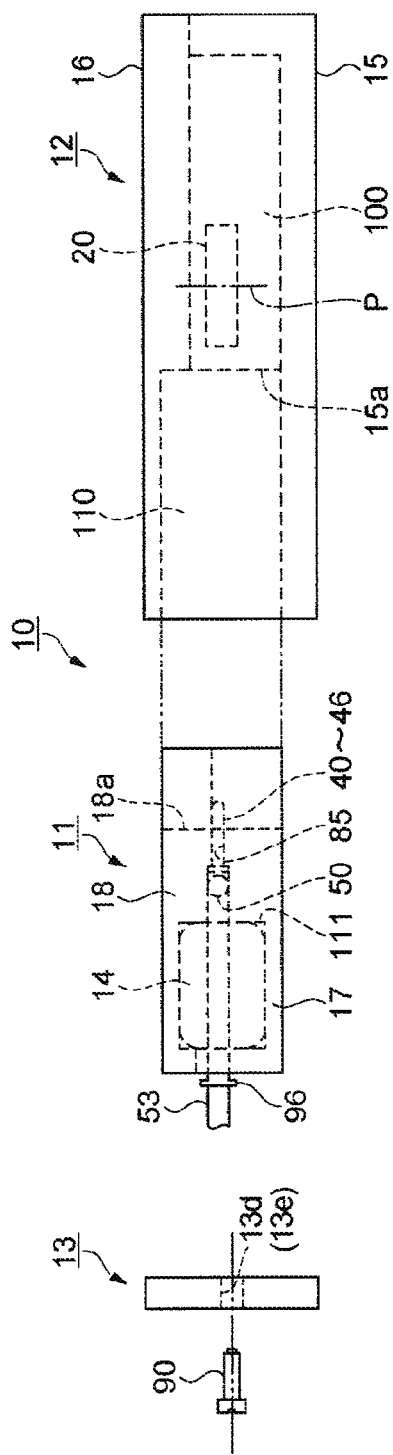

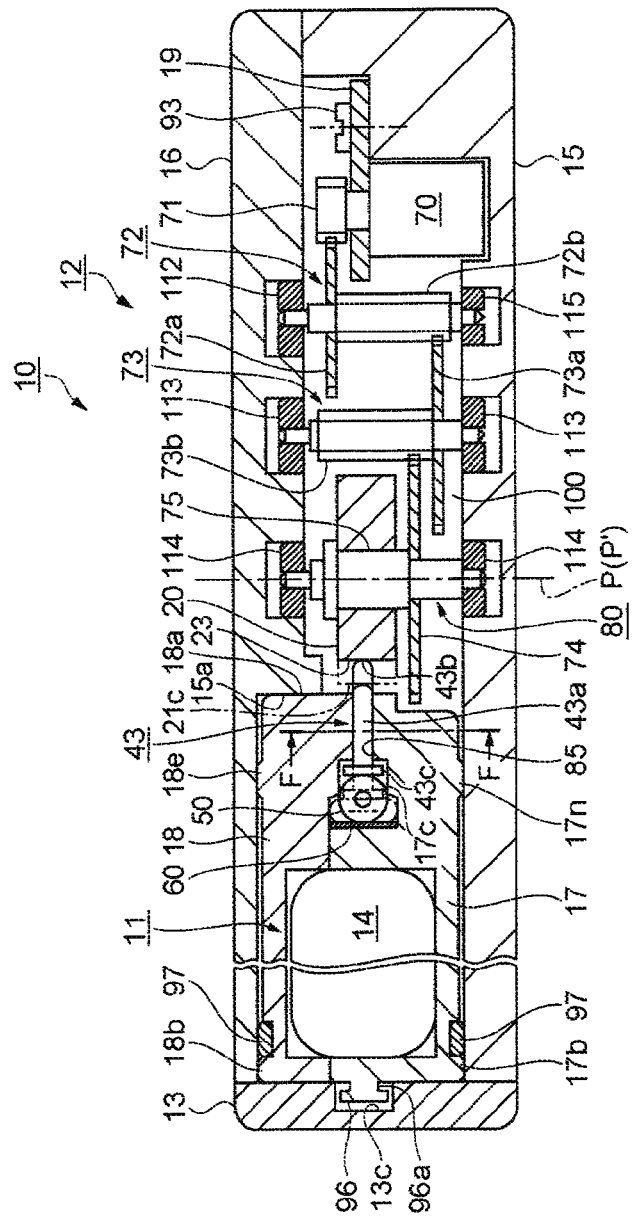
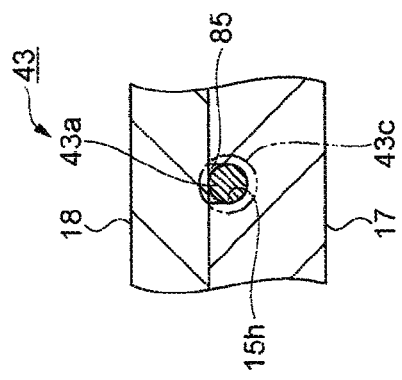
FIG. 6A
FIG. 6B

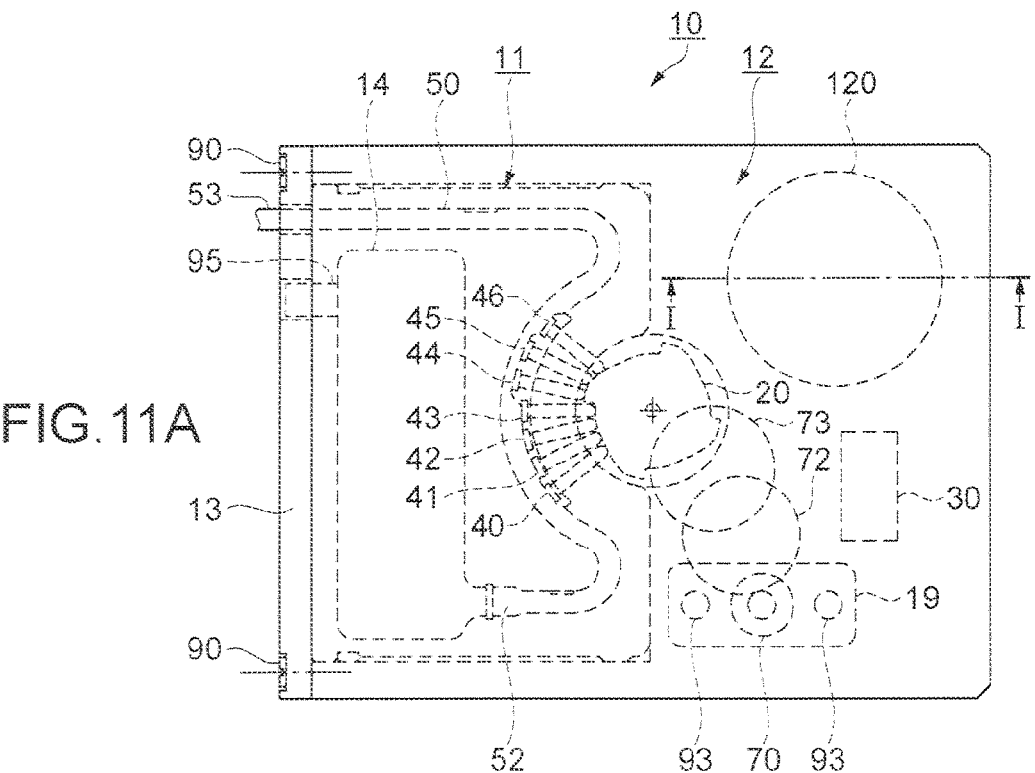
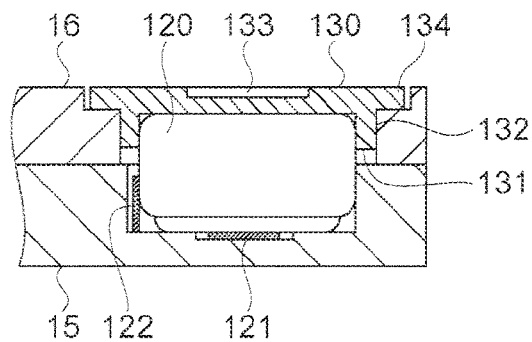
FIG.11A
FIG.11B

CONTROL UNIT, TUBE UNIT, AND MICROPUMP

CROSS REFERENCE TO RELATED APPLICATIONS

This application is a divisional of U.S. patent application Ser. No. 12/542,751 filed on Aug. 18, 2009. This application claims the benefit of Japanese Patent Application No. 2008-249798 filed Sep. 29, 2008. The disclosures of the above applications are incorporated herein by reference.

BACKGROUND

1. Technical Field

The present invention relates to a tube unit, a control unit, and a micropump configured with them mounted thereon.

2. Related Art

As an apparatus which transports a liquid at a low speed, there is a peristaltic drive type pump. As the peristaltic drive type pump, a structure is known in which a rotor including a plurality of rollers is rotated with a step motor as a drive source, and the rotor rotates along a soft tube while causing the plurality of rollers to roll, carrying out a suction and discharge of a liquid (for example, Japanese Patent No. 3,177,742).

This kind of pump has a configuration wherein a pump module including a tube and a rotor pressing and closing the tube, and a motor module including a step motor and an output gear mechanism, are assembled stacked one on the other, a gear acting as a coupling element is provided on the rotating shaft of the rotor, a pinion acting as a power extraction mechanism is provided on the output gear mechanism and, when the pump module and motor module are connected stacked one on the other, by causing the pinion and gear to mesh with each other, a rotary drive force of the step motor is transmitted to the rotor.

This kind of peristaltic drive type pump of Japanese Patent No. 3,177,742 has a problem in that, as the tube is always pressed and closed by the roller after the pump has been manufactured, in the event that there is a long period from the pump being manufactured (assembled) until it is used, the tube deteriorates, and a liquid discharge accuracy cannot be secured.

Also, it is conceivable that, when the pump module and motor module are mounted stacked one on the other, as the structure causes the pinion and gear to mesh with each other, in the event that their teeth are out of phase with each other, the pinion and gear overlap each other, and are broken.

SUMMARY

The invention can be realized as the following embodiments or application examples.

Application Example 1

A micropump according to this application example includes a tube unit including an elastic tube, one portion of which is disposed in an arc shape, a plurality of fingers, which are disposed radially from the direction of the radius point of the arc shape of the tube, and a guide frame, which holds the tube and the plurality of fingers; a control unit including a cam, which presses the plurality of fingers in order from the inflow side to the outflow side of the tube, a drive section, which applies torque to the cam, a control circuit, which carries out a drive control of the drive section, and a machine casing, which holds the cam, drive section, and control circuit; a reservoir with which a flow inlet of the tube communicates; and a power source which supplies electric power to the control circuit. The tube unit is removably mounted in the control unit in a direction approximately parallel to the plane of rotation of the cam.

It is conceivable that, on the tube continuing to be in a pressed and closed condition for a long period, the resilience of the tube deteriorates, and a discharge accuracy decreases. However, according to this application example, as the tube unit is separable from the control unit including the cam which presses the plurality of fingers which press and close the tube, in a condition in which the tube unit is alone, the tube is maintained in an opened condition. For this reason, it is possible to prevent the decrease in discharge accuracy accompanying the deterioration in resilience due to the continuous pressure and closure of the tube, and maintain a desired discharge accuracy.

Also, it is conceivable that the resilience of the tube deteriorates by repeating the pressure and closure, and opening, of the tube for a long time, in which kind of case a tube replacement is needed, but it is possible to easily replace the tube as the tube unit after a certain time of use.

Also, as the cam and drive section are configured as the control unit, when the tube unit and control unit are mounted, it is not necessary that the kinds of pinion and gear in the previously described heretofore known technology are connected in mesh, meaning that there is no damage in a meshing process.

Also, in the event that the tube unit is mounted in the control unit in a direction parallel thereto, it is possible to place the plurality of fingers into a condition in which they can press the tube. Consequently, no connection mechanism being needed between the motor module and pump module as in the heretofore known technology, it is possible to simplify the structure, it is possible to improve an assembling property, and furthermore, it is possible to realize a reduction in thickness.

Also, it is possible to make the tube unit far lower in cost than the control unit including the cam, drive section, and control circuit. Therein, in the event that the tube unit including the tube making direct contact with a chemical or the like is used once and thrown away, and the control unit is repeatedly used, it is possible to reduce a running cost.

Application Example 2

In the micropump according to the above mentioned application example, it is preferable that the tube unit is mounted inside a space provided in the machine casing.

According to this kind of configuration, the machine casing configuring the control unit has a casing function, eliminating a need for a casing for housing the tube unit and control unit, enabling the simplification in structure and the reduction in thickness.

Application Example 3

In the micropump according to the above mentioned application example, it is preferable that guide portions, which cause the radius point of the arc shape of the tube to approximately coincide with the rotation center of the cam when the tube unit is mounted in the control unit, are provided one in each of the tube unit and the control unit.

The micropump of the above mentioned application example is configured so that the plurality of fingers are pressed by the rotation of the cam, pressing and closing the tube. Consequently, it is necessary to cause the radius point of the arc shape of the tube to approximately coincide with the rotation center of the cam.

Because of this, when the tube unit is mounted in the control unit, by providing the guide portions one in each of them, it is possible to cause the radius point of the arc shape of the tube to coincide with the rotation center of the cam, and all of the plurality of fingers can reliably carry out the pressure and closure of the tube without providing a dedicated position regulation member.

Application Example 4

In the micropump according to the above mentioned application example, it is preferable that a detector, which detects that the radius point of the arc shape of the tube has coincided with the rotation center of the cam when the tube unit is mounted in the control unit, is provided between the tube unit and the control unit.

According to this kind of configuration, by enabling the drive of the drive section in the event that it is detected by the detector that the radius point of the arc shape of the tube and the rotation center of the cam have been caused to coincide, the drive is carried out when in a condition in which all of the plurality of fingers have the same amount of pressure and closure, meaning that it is possible to transport the liquid at a desired flow per unit time.

Application Example 5

In the micropump according to the above mentioned application example, it is preferable that it further includes a cover member for fixing the tube unit to the control unit, and that an elastic member, which biases the tube unit toward the control unit in a direction in which the radius point of the arc shape of the tube is caused to approximately coincide with the rotation center of the cam, is provided between the cover member and the tube unit.

It is conceivable that, when the tube unit is fixed to the control unit using the cover member, a horizontal space occurs between the tube unit and control unit due to a variation in dimension of component parts, and the tube will not be able to be pressed and closed by the fingers.

Therein, by biasing the tube unit in the direction of the control unit by means of the elastic member, it is possible to bring the guide portion of the tube unit into firm abutment with the guide portion of the control unit, and cause the radius point of the arc shape of the tube to coincide with the rotation center of the cam, enabling each of the plurality of the fingers to reliably press and close the tube.

Application Example 6

In the micropump according to the above mentioned application example, it is preferable that the biasing force of the elastic member is greater than the pressure of the plurality of fingers against the tube.

By so doing, when the fingers press the tube, the tube unit (that is, the tube) does not move in a direction away from the fingers due to the pressure of the fingers, meaning that it is possible to reliably press and close the tube.

Application Example 7

In the micropump according to the above mentioned application example, it is preferable that one portion, or the whole, of the machine casing and the guide frame is transparent.

By making the machine casing and guide frame transparent, it is possible to observe the internal component parts or an engagement relationship and drive condition of each component part. It is possible to detect therefrom whether the condition is normal, where there is a problem, or the like. Furthermore, it is possible to observe the amount of liquid in the reservoir. It is sufficient that a range made transparent is a range of a portion desired to be observed.

Application Example 8

In the micropump according to the above mentioned application example, it is preferable that the power source is housed in the tube unit.

As the power source, in order to realize a reduction in size of the micropump, it is preferable to employ, for example, a small button type battery or a sheet type battery.

When changing a chemical in use, or when replacing a used tube, by replacing a battery together with the tube as the tube unit, it is possible to prevent a battery capacity from running short during use.

Application Example 9

In the micropump according to the above mentioned application example, it is desirable that the power source is removably mounted in the tube unit.

In the event of using a small battery as the power source, it is expected that the battery capacity runs short during use. Therein, by adopting a configuration capable of easily replacing the battery alone, it is possible to continue to use the micropump over a long time.

Application Example 10

In the micropump according to the above mentioned application example, it is preferable that the reservoir is detachably attached to the tube.

It is conceivable that a chemical stored in the reservoir runs short when the micropump is used. Therein, by adopting a configuration such that the reservoir is attachable to and detachable from the tube, it is possible to remove a reservoir in which there is little chemical, connect a reservoir with a chemical stored therein to the tube, and use the micropump over a long time.

Application Example 11

In the micropump according to the above mentioned application example, it is preferable that the reservoir is housed in the tube unit.

By so doing, in the event that the tube unit including the tube is replaced at a point at which the liquid in the reservoir has run out, it is possible to replace the tube as the tube unit before a deterioration of the tube considered to occur by repeating the pressure and closure, and opening, of the tube for a long time, and it is possible to increase a reliability of the micropump.

Application Example 12

In the micropump according to the above mentioned application example, it is preferable that the reservoir and the power source are housed in the tube unit.

The tube unit is mounted in the machine casing of the control unit. Consequently, the fact that the reservoir and power source are both provided inside the tube unit means that they are housed in the control unit.

This kind of configuration meaning that a substantial function necessary for the micropump is housed in the machine casing, as well as the reduction in size being possible, the micropump is easy to handle as it has no parts projecting from the machine casing, and in addition, it is suitable for a case in which it is used mounted in a living organism.

Also, as it is possible to replace the battery as the tube unit in accordance with a reservoir replacement time or a tube replacement time, it is possible to further increase the reliability.

Furthermore, in the event that the battery is provided outside the micropump, a long lead for a connection and a battery casing are needed but, according to this application example, there is an advantage in that they are not needed.

Application Example 13

In the micropump according to the above mentioned application example, it is desirable that the reservoir includes a port for injecting a fluid thereinto, or sealing it therein.

Herein, as the port, it is possible to employ, for example, a septum.

By providing the septum on the reservoir, it is possible to easily carry out the injection of the fluid into the reservoir in a condition in which the reservoir is connected to the tube.

Application Example 14

In the micropump according to the above mentioned application example, it is desirable that the reservoir is housed in the tube unit, and that the port is closely held to an opening provided in the guide frame, and disposed in such a way as to expose a flow inlet of the port to the outside of the guide frame.

According to this kind of configuration, it is possible to easily carry out an additional injection of the fluid into the reservoir in the condition in which the tube unit is alone. Also, it is also possible to easily carry out the additional injection of the fluid in the condition in which the tube unit is mounted in the control unit. Furthermore, it is also possible to easily carry out the injection of the fluid in a condition in which the micropump is in use.

By closely fixing the port to the tube guide frame, it is possible to prevent an intrusion of the fluid from a space between the port and tube guide frame into the interior of the tube unit.

Application Example 15

In the micropump according to the above mentioned application example, it is desirable that an air vent filter for blocking a passage of air bubbles is provided in a communication portion between the reservoir and the tube.

It may happen that air merges into the fluid stored in the reservoir, and it is conceivable that the merging air gathers and turns to air bubbles as time elapses. When a liquid, is a chemical, and is discharged into a living organism, in the event of injecting it including air bubbles, it may happen that there occurs an effect which cannot be overlooked.

Therein, by providing the air vent filter for allowing the liquid to pass, and blocking the passage of the air bubbles, through the communication portion between the reservoir and tube, it is possible to suppress the air bubbles intruding into the living organism, and it is possible to increase safety.

Application Example 16

In the micropump according to the above mentioned application example, it is preferable that the power source is housed in the control unit.

With this kind of configuration, by housing the power source in the control unit, it is possible to easily carry out the connection of the control circuit and power source.

Also, by disposing the power source in a space other than a range in which the tube unit is mounted, it is possible to make the power source thicker than with the structure in which the power source is mounted in the tube unit, meaning that it is possible to employ a battery with a larger capacity.

Furthermore, as a vacant space increases in the tube unit, it is possible to increase the liquid capacity of the reservoir by that amount.

Application Example 17

In the micropump according to the above mentioned application example, it is desirable that the power source is mountable in and removable from the control unit.

By so doing, it is also possible to replace the power source in the condition in which the tube unit is mounted in the control unit.

Application Example 18

A control unit according to this application example, being mountable in and removable from a tube unit including an elastic tube, one portion of which is disposed in an arc shape, a plurality of fingers, which are disposed radially from the direction of the radius point of the arc shape of the tube, and a guide frame, which holds the tube and the plurality of fingers, includes a cam, which presses the plurality of fingers in order from the inflow side to the outflow side of the tube; a drive section, which applies torque to the cam; a control circuit, which carries out a drive control of the drive section; and a machine casing, which holds the cam, the drive section, and the control circuit.

According to the configuration of this application example, the control unit is configured including drive related components such as the drive section, cam, and control circuit. Consequently, it is possible to carry out a drive confirmation as the control unit. Also, there being no need for a coupling mechanism between the drive related components, it is possible to attain a use condition immediately by slidingly mounting the tube unit.

Application Example 19

In the control unit according to the above mentioned application example, it is desirable that a power source which supplies electric power to the control circuit is removably mounted therein.

With this kind of configuration, by housing the power source in the control unit, it is possible to easily carry out the connection of the control circuit and power source.

Also, by so doing, it is also possible to carry out the replacement of the power source in a condition in which the control unit is alone, or in the condition in which the tube unit is mounted in the control unit.

Application Example 20

A tube unit according to this application example, being mountable in and removable from a control unit including a cam, a drive section, which applies torque to the cam, a control circuit, which carries out a drive control of the drive section, and a machine casing, which holds the cam, drive section, and control circuit, includes a tube, which is disposed in such a way that the rotation center of the cam approximately coincides with the center of the arc shape of the tube; a plurality of fingers, which are disposed radially from the direction of the rotation center of the cam; and a guide frame, which holds the tube and the plurality of fingers.

According to this application example, in the condition in which the tube unit is alone, the tube is maintained in an opened condition, meaning that it is possible to prevent a decrease in discharge accuracy due to a deterioration in resilience involved in holding the tube in a pressed and closed condition.

Also, it is possible to make the tube unit far lower in cost than the control unit including high cost components such as the cam, drive section, and control circuit. Consequently, in the event that the tube unit including the tube making direct contact with a chemical is used once and thrown away, it is possible to reduce the running cost.

Application Example 21

In the tube unit according to the above mentioned application example, it is preferable that the guide frame includes finger guide slots communicating with a tube guide groove in which the tube is inserted, and that each of the plurality of fingers includes a shaft, which is inserted in the finger guide slot, and a flange shaped tube pressing portion which, being larger than the diameter of the finger guide slot, abuts against the tube.

By so doing, in the condition in which the tube unit is alone, the tube pressing portions have a function of pressing and closing the tube, and a function of positioning an advance and withdrawal of the fingers, and it is possible to prevent the fingers from falling off the finger guide slots.

Application Example 22

In the tube unit according to the above mentioned application example, it is preferable that a reservoir communicating with a flow inlet of the tube is housed therein.

By housing the reservoir inside the tube unit, it becomes easier to handle the tube unit including the reservoir. Also, as the reservoir and tube are connected inside the tube unit, it is possible to shorten the tube.

Application Example 23

In the tube unit according to the above mentioned application example, it is preferable that a power source which supplies electric power to the control circuit is housed therein.

As the power source, in order to realize a reduction in size of the tube unit, for example, a small button type battery or a thin sheet type battery is employed.

When changing a chemical in use, or when replacing a tube used for a long period, it being possible to replace a battery together with the tube as the tube unit, it is possible to prevent a battery capacity from running short during use.

Application Example 24

In the tube unit according to the above mentioned application example, it is desirable that a reservoir, which communicates with the flow inlet of the tube, and a power source, which supplies electric power to the control circuit, are housed therein.

According to this kind of configuration, as it is possible to replace the battery as the tube unit in accordance with the reservoir replacement time or tube replacement time, it is possible to further increase the reliability.

BRIEF DESCRIPTION OF THE DRAWINGS

The invention will be described with reference to the accompanying drawings, wherein like numbers reference like elements.

FIGS. 4A to 4C are exploded front views of the micropump according to Embodiment 1.

FIG. 6A is a sectional view showing the A-P-A' section of FIG. 5, and FIG. 6B is a sectional view showing the F-F section of FIG. 6A.

FIG. 8A is a partial plan view, and FIG. 8B is a sectional view showing the E-E section of FIG. 8A.

FIG. 9A is a partial plan view, and FIG. 9B is a sectional view showing the G-G section of FIG. 9A.

FIG. 10A is a partial plan view, and FIG. 10B is a sectional view showing the H-H section of FIG. 10A.

FIGS. 11A and 11B showing one portion of a micropump according to Embodiment 5, FIG. 11A is a partial plan view, and FIG. 11B is a sectional view showing the I-I section of FIG. 11A.

DESCRIPTION OF EXEMPLARY EMBODIMENTS

Hereafter, a description will be given, based on the drawings, of embodiments of the invention.

Figure 7:
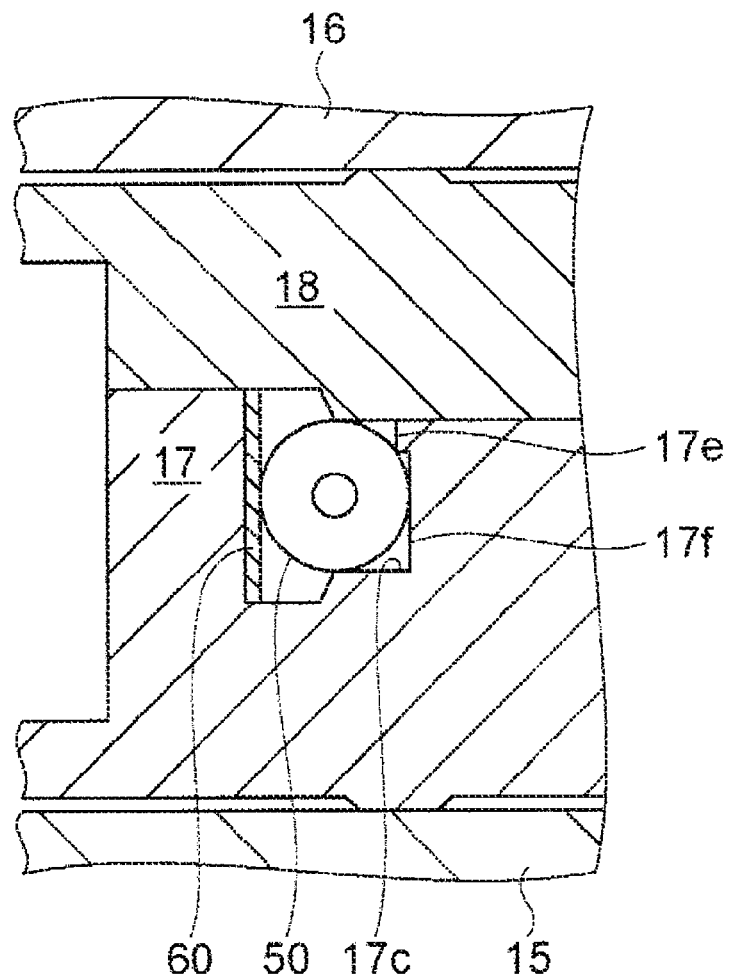
FIG. 7 is a fragmentary sectional view showing a tube holding structure of the micropump according to Embodiment 1.
Figure 8A:
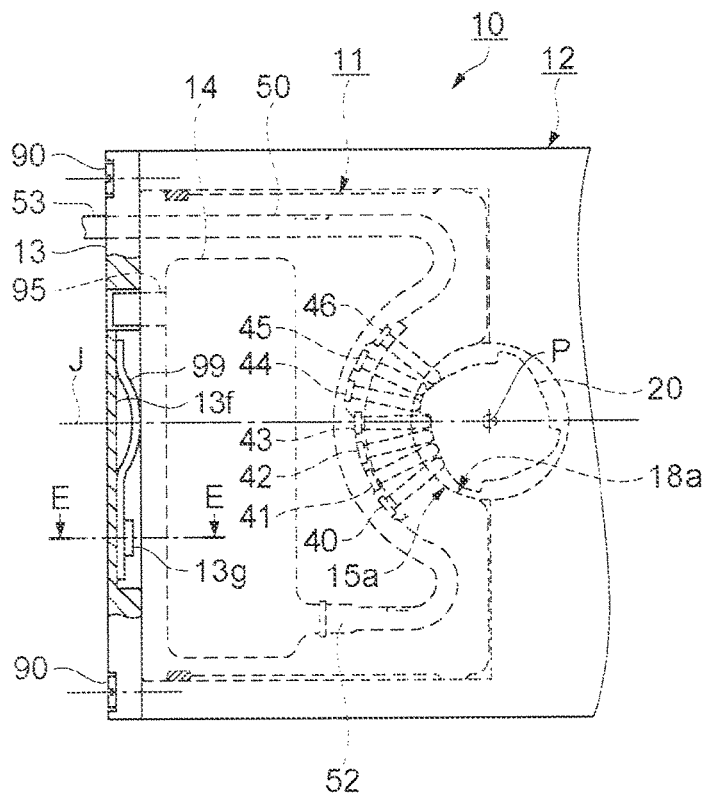
FIGS. 8A and 8B showing one portion of a micropump according to Embodiment 2.
Figure 8B:
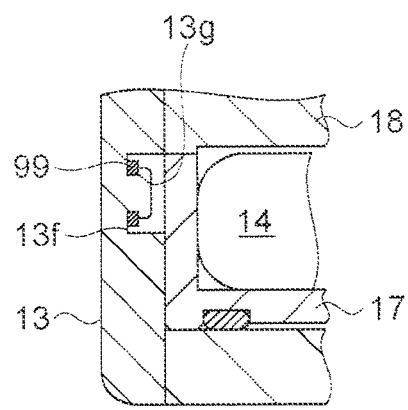
Figure 9A:
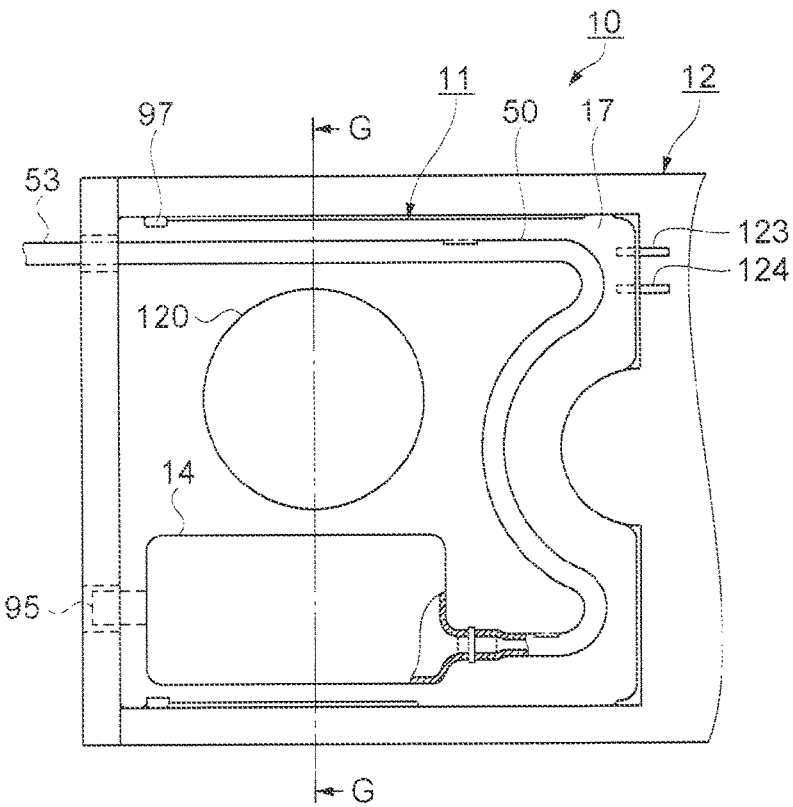
FIGS. 9A and 9B showing one portion of a micropump according to Embodiment 3.
Figure 9B:
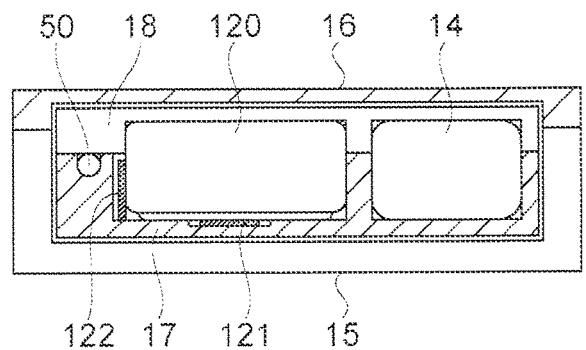
Figure 10A:
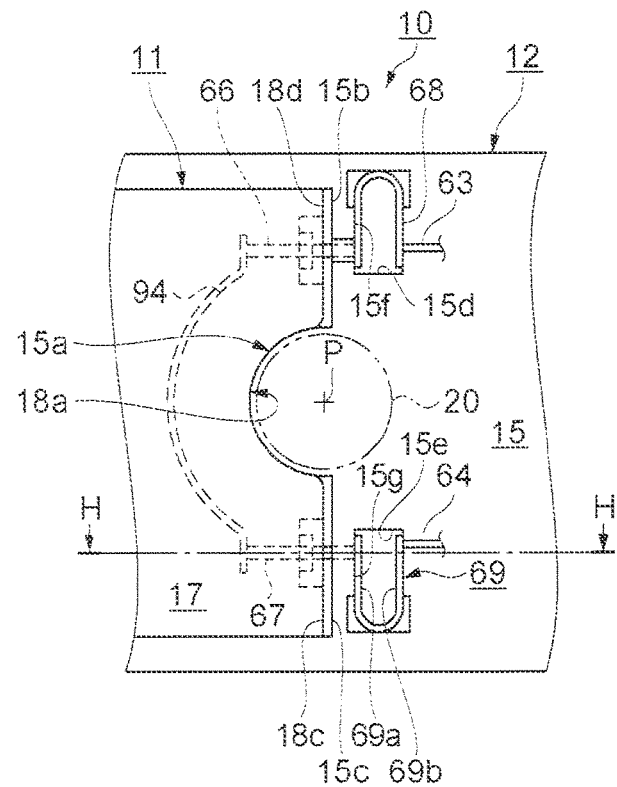
FIGS. 10A and 10B showing one portion of a micropump according to Embodiment 4.
Figure 10B:
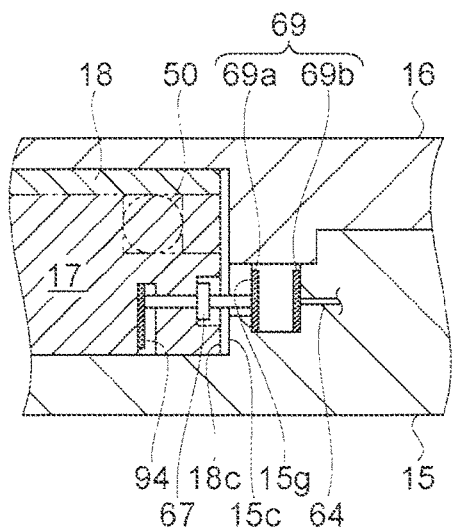

FIGS. 1 to 7 show a micropump of Embodiment 1, FIGS. 8A and 8B show Embodiment 2, FIGS. 9A and 9B Embodiment 3, FIGS. 10A and 10B Embodiment 4, and FIGS. 11A and 11B Embodiment 5.

The drawings to be referred to in the following description are schematic diagrams in which the vertical and horizontal scales of members and portions differ from actual ones, for the convenience of illustration.

Embodiment 1

Figure 1:
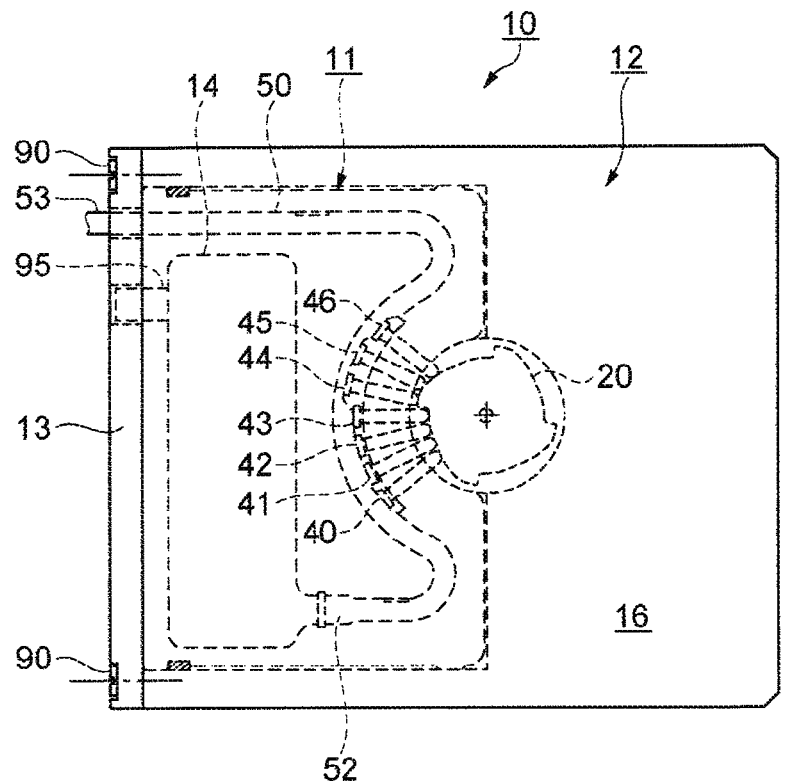
FIG. 1 is a schematic plan view showing a micropump according to Embodiment 1.
Figure 2:
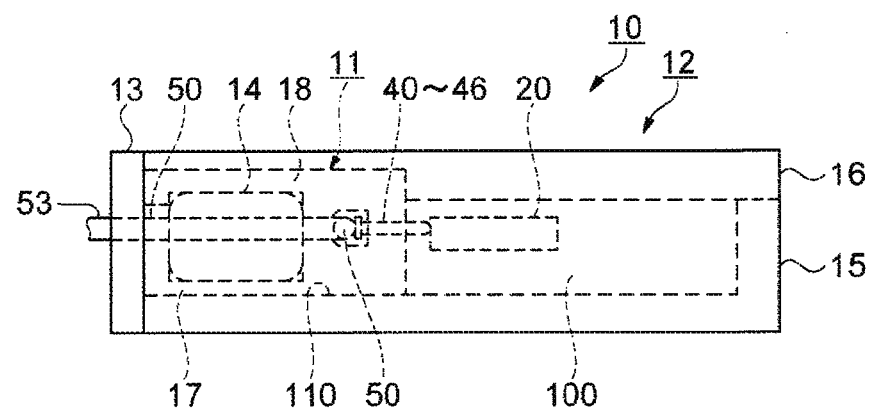
FIG. 2 is a schematic front view showing the micropump according to Embodiment 1.

FIG. 1 is a schematic plan view showing the micropump according to Embodiment 1, and FIG. 2 is a schematic front view. In FIGS. 1 and 2, the micropump 10 is integrally configured so that a tube unit 11 is slidingly inserted into a space 110 through an opening in a side surface of a control unit 12 on the left side as seen in the drawings, mounted in the control unit 12, and fixed to the control unit 12 with fixing screws 90 by a fixing frame 12 acting as a cover member.

The tube unit 11 is configured of an elastic tube 50, one portion of which is disposed in an arc shape, a first tube guide frame 17 and second tube guide frame 18 which, acting as guide frames, hold the tube 50, a reservoir 14 which, having a flow inlet 52 of the tube 50 communicating therewith, stores a liquid, and a plurality of fingers 40 to 46. Hereafter, a description will be given, representing a fluid as a liquid such as a chemical.

The control unit 12 is configured including a cam 20, a motor and transmission mechanism which, acting as a drive section, applies torque to the cam 20, and a control circuit which carries out a drive control of the motor (the illustration of the motor, transmission mechanism, and control circuit is omitted).

The cam 20, motor, transmission mechanism, fingers 40 to 46, and control circuit are held inside a space 100 formed by a first machine casing 15 and second machine casing 16 which act as machine casings.

Also, one extremity of the tube 50 being a flow outlet 53, the flow outlet 53, passing through the fixing frame 13, and being protruded outward, discharges the liquid from the reservoir 14 to the exterior.

A septum 95, which acts as a port for injecting the liquid into, or sealing it in, the reservoir 14, is provided in one portion of the reservoir 14. The septum 95 is protruded inwardly of the fixing frame 13.

Continuing, a description will be given of configurations of, and a method of assembling, the tube unit 11, control unit 12, and fixing frame 13.

Figures 3A, 3B, 3C:
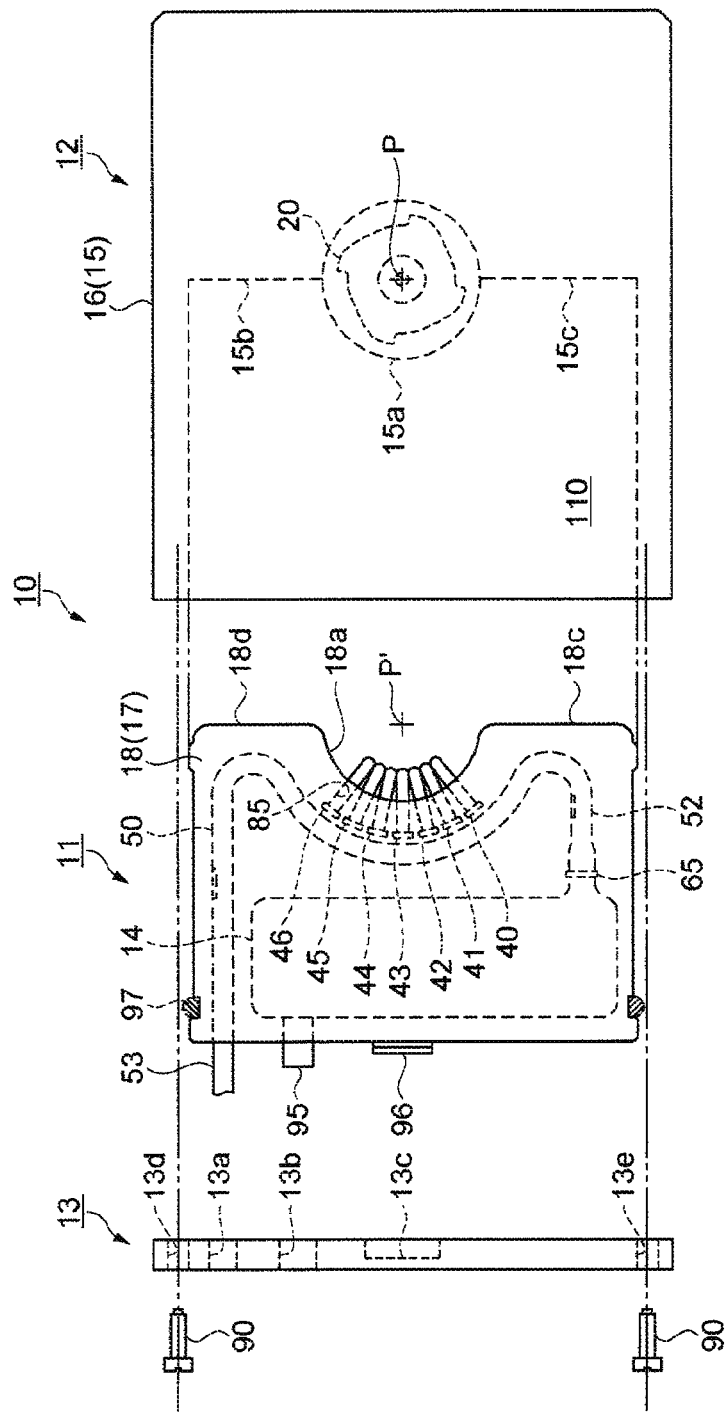
FIGS. 3A to 3C are exploded plan views of the micropump according to Embodiment 1.

FIGS. 3A to 3C are exploded plan views of the micropump, and FIGS. 4A to 4C are an exploded front view. In FIGS. 3A to 4C, A shows the fixing frame 13, B the tube unit 11, and C the control unit 12.

As shown in FIGS. 3A to 4C, in the control unit 12, the spaces 100 and 110 are configured by the first machine casing 15 and second machine casing 16. The cam 20, motor, transmission mechanism, and control circuit (the illustration of the last three is omitted) are disposed in the space 100, and the space 110 which has an opening on one side is a space in which the tube unit 11 is mounted.

The fingers 40 to 46 are inserted in finger guide slots 85 (provided corresponding one to each of the fingers 40 to 46) formed by the first tube guide frame 17 and second tube guide frame 18. Extremities on one side of the fingers 40 to 46 are protruded in the direction of the space 110, while the other extremities are protruded in a direction in which they abut against the tube 50 and, when the tube unit 11 is mounted in the control unit 12, the fingers 40 to 46 attain a condition in which they can press and close the tube 50.

The tube 50 and reservoir 14 are connected by a communication member, and the tube unit 11, in a condition in which it is held by the first tube guide frame 17 and second tube guide frame 18, is mounted in the space 110 of the control unit 12 from the left side as seen in the drawings.

The cam 20 rotates with a rotation center P as its axis. The tube unit 11 is mounted in the control unit 12 so as to be parallel to the plane of rotation of the cam 20.

Also, a packing 97 is fitted along an outer peripheral surface in the fixing frame 13 side vicinity of the tube unit 11, and the space 110 is hermetically sealed in a condition in which the tube unit 11 is inserted in the control unit 12.

Also, the tube unit 11 is pushed into the control unit 12 until a concave wall surface 18a abuts against a wall surface 15a of the control unit 12 protruded in an arc shape. The wall surfaces 15a and 18a are formed mutually concentric with the rotation center P of the cam 20.

Figure 5:
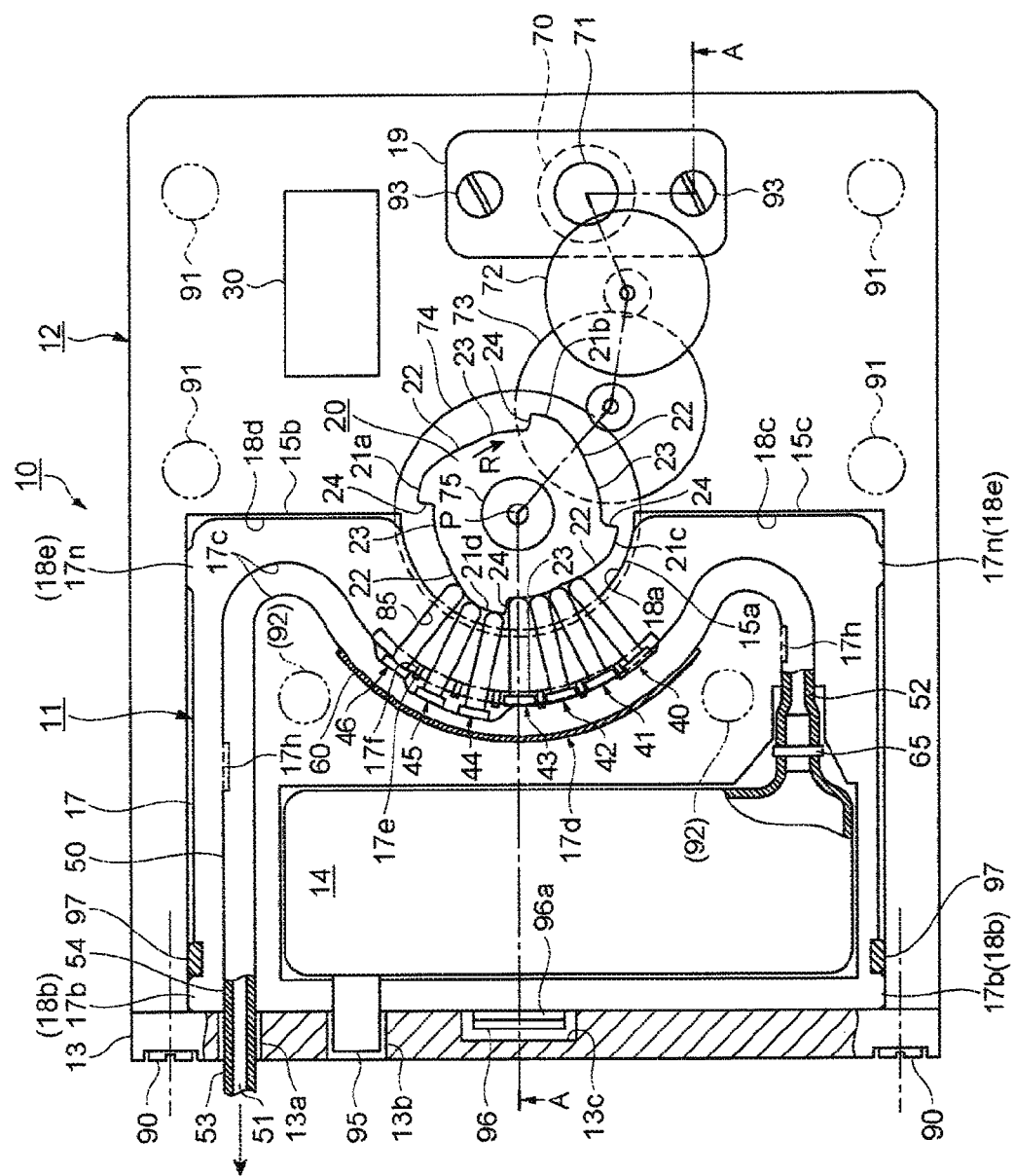
FIG. 5 is a plan view of the micropump according to Embodiment 1.

Herein, in a condition in which the wall surface 15a and wall surface 18a are in abutment with each other, the dimension of the control unit side extremities 18c and 18d of the tube unit 11 is set in such a way that a space is left between themselves and inner side walls 15b and 15c of the control unit 12 (refer also to FIG. 5).

The space is provided in order to bring the wall surface 15a and wall surface 18a into firm abutment, and cause a radius point P' of an arc shaped portion (a range pressed by the fingers 40 to 46) of the tube 50 to coincide with the rotation center P of the cam 20.

After the tube unit 11 is inserted into the control unit 12, the fixing frame 13 is mounted from the direction of the tail of the tube unit 11 (the opening side of the space 110). Specifically, the fixing screws 90 are inserted into through holes 13d and 13e opened in the fixing frame 13, and threaded and fixed in screw holes (not shown) provided in the first machine casing 15 of the control unit 12.

The flow outlet 53 of the tube 50, and the septum 95 provided on the reservoir 14, being protruded from the tube unit 11, when the fixing frame 13 is fixed, the tube 50 and the septum 95 are respectively inserted into a tube insertion hole 13a and a septum insertion hole 13b, and the flow outlet 53 is protruded and extended outwardly of the fixing frame 13.

A protrusion 96 is formed on a side surface of the first tube guide frame 17 on the fixing frame 13 side. The protrusion 96 is used when removing the tube unit 11 from the control unit 12. The protrusion 96 is housed inside a recess 13c bored in the fixing frame 13.

Continuing, a description will be given, referring to the drawings, of a configuration and operation of each component of the micropump 10 assembled in the way heretofore described.

FIGS. 5 to 7 showing the micropump according to the embodiment, FIG. 5 is a plan view, FIG. 6A a sectional view showing the A-P-A' section of FIG. 5, FIG. 6B a sectional view showing the F-F section of FIG. 6A, and FIG. 7 a fragmentary sectional view showing a tube holding structure. Firstly, a description will be given, referring to FIGS. 5 and 6, of a configuration of the drive section. FIG. 5 represents the second machine casing 16 and second tube guide frame 18 in perspective.

The drive section, including a step motor 70 as the motor, transmits a rotation of the step motor 70 to a cam drive gear 74 via the transmission mechanism (configured of a motor gear 71, first transmission wheel 72, and second transmission wheel 73).

The step motor 70 is held by a motor support frame 19, and fixed to the first machine casing 15 by fixing screws 93. The step motor 70 includes the motor gear 71.

The first transmission wheel 72 and second transmission wheel 73 are rotatably journaled by the first machine casing 15 and second machine casing 16.

The first transmission wheel 72 is journaled by a bearing 115 provided in the first machine casing 15, and a bearing 112 provided in the second machine casing 16, in a condition in which a transmission gear 72a is journaled on a pinion 72b.

The second transmission wheel 73 is journaled by a bearing 113 provided in the first machine casing 15, and a bearing 113 provided in the second machine casing 16, in a condition in which a transmission gear 73a is journaled on a pinion 73b.

Also, a cam drive gear 74, configuring a cam drive wheel 80 by, together with the cam 20, being journaled on a cam shaft 75, is journaled by a bearing 114 provided in the first machine casing 15, and a bearing 114 provided in the second machine casing 16. Between the motor gear 71 and cam drive gear 74, as well as the gear ratio of each gear being set, a predetermined rotary speed and rotary torque of the cam 20 are set, in such a way as to provide a deceleration drive.

The step motor 70, first transmission wheel 72, second transmission wheel 73, and cam drive wheel 80 are disposed in the space 100 configured by the first machine casing 15 and second machine casing 16. The bonding surfaces of the first machine casing 15 and second machine casing 16 are closely bonded together.

As a first machine casing 15 and second machine casing 16 bonding structure, it is possible to employ a structure in which they are fixed using kinds of fixing screw 91 shown in FIG. 5, a structure in which the bonding surfaces thereof are welded or adhesively attached together, or the like.

Also, the control circuit 30, being provided in the control unit 12, is connected to the step motor 70 via a circuit pattern provided on an unshown circuit substrate, causing the step motor 70 to rotate at a predetermined rotary speed.

The cam 20 having concavities and convexities in an outer circumferential direction, finger pressing surfaces 21a to 21d are formed on the outermost periphery. The finger pressing surfaces 21a to 21d are formed on a concentric circle equidistant from the rotation center P.

Also, the circumferential pitches and contours of the finger pressing surface 21a and finger pressing surface 21b, the finger pressing surface 21b and finger pressing surface 21c, the finger pressing surface 21c and finger pressing surface 21d, and the finger pressing surface 21d and finger pressing surface 21a, are formed equal to each other.

Each of the finger pressing surfaces 21a to 21d is formed continuous with a finger pressing slope 22 and an arc portion 23 on a concentric circle having the rotation center P as its center. The arc portions 23 are provided in positions in which they do not press the fingers 40 to 46.

Also, the extremities of the finger pressing surfaces 21a, 21b, 21c, and 21d, and the arc portions 23, are connected by linear portions 24 extended from the rotation center P.

Next, a description will be given, referring to FIGS. 5, 6A, and 6B, of a configuration of the tube unit 11. The tube 50, one portion of which facing the cam 20 has the arc shape, is mounted in a tube guide groove 17c formed in the first tube guide frame 17.

The radius point P' (refer to FIGS. 3A to 3C) of the arc shape of the tube 50 coincides with the rotation center P of the cam 20 in the condition in which the tube unit 11 is mounted in the control unit 12. The one extremity of the tube 50 communicates with the reservoir 14, and the other extremity is the flow outlet 53 extended through the tube insertion hole 13a in the fixing frame 13.

The fingers 40 to 46 are inserted in the finger guide slots 85 formed by the first tube guide frame 17 and second tube guide frame 18. The finger guide slots 85, being provided corresponding one to each of the fingers 40 to 46, are equally spaced and extended radially from the rotation center P of the cam 20 (that is, coinciding with the arc radius point P' of the tube 50).

As the fingers 40 to 46 are formed in the same shape, a description will be given exemplifying with the finger 43.

As shown in FIG. 6B, the finger guide slot 85 is configured by sealing an opening on the upper side, as seen in the drawing, of an approximately U-shaped groove 15h formed in the first tube guide frame 17, with the second tube guide frame 18. The finger guide slot 85 penetrates from the tube guide groove 17c to the wall surface 18a.

As shown in FIG. 6A, the finger 43 is configured of a columnar shaft 43a, a flange shaped tube pressing portion 43c provided at one extremity of the shaft 43a, and a cam abutment portion 43b obtained by rounding the other extremity into a hemisphere.

The diameter of the tube pressing portion 43c is set larger than the diameter of the finger guide slot 85, regulating an axial movement of the finger 43, preventing the finger 43 from falling off the tube unit 11.

After the shaft 43a of the finger 43 is mounted in the groove 15h from the direction of the opening, the second tube guide frame 18 is mounted on the first tube guide frame 17 from above, thereby regulating a position of the finger 43 in a sectional direction.

Nearly the whole of the tube 50 is mounted in the tube guide groove 17c, thereby regulating a plan position of the tube 50, and also, a protrusion acting as a tube holding portion is formed in one portion of the side wall of the tube guide groove 17c, thus restricting a levitation of the tube 50.

FIG. 7 is a fragmentary sectional view showing the tube holding structure. FIG. 7 illustrates it exemplifying with a protrusion between the finger 45 and finger 46, from among protrusions between adjacent ones of the fingers 40 to 46 (refer also to FIG. 5).

In the tube guide groove 17c, a tube guide side wall 17f, acting as a protrusion with a width such as not to interfere with an advance and withdrawal of the fingers 45 and 46, is provided between the finger 45 and finger 46, and a kind of protrusion 17e protruding over one upper portion of the tube 50 is formed in an upper portion of the tube guide side wall 17f.

In this way, by the tube guide side wall 17f and protrusion 17e being provided between adjacent fingers, the tube position regulation in the plan direction and the suppression of the levitation of the tube are carried out in a range in which the fingers 40 to 46 are disposed.

In the embodiment, as shown in FIG. 5, protrusions 17h having the same function as the protrusions 17e are provided in a position close to the flow outlet 53 of the tube, and in a position close to the flow inlet 52 too.

In a condition in which the tube 50, reservoir 14, and fingers 40 to 46 are mounted on the first tube guide frame 17, the first tube guide frame 17 and second tube guide frame 18, the bonding surfaces thereof being closely bonded together, are fixed using fixing screws 92, thereby configuring the tube unit 11.

A space between the tube guide groove 17c and tube 50, in the vicinity of the flow outlet 53 of the tube 50, is hermetically sealed using a packing, an adhesive, or the like, in a condition in which the first tube guide frame 17 and second tube guide frame 18 are fixed. By so doing, a hermetically sealed structure is established inside the tube unit 11.

Also, the packing 97 being fitted over the outer periphery of the tube unit 11 in the vicinity of the fixing frame 13, in the condition in which the tube unit 11 is inserted in the control unit 12, the interior is made a hermetically sealed space, providing the micropump 10 with a waterproof structure and a dust-proof structure.

In the event that it is sufficient that the micropump 10 is of a non-waterproof structure, the packing 97 is unnecessary.

Also, at least in a plan range of the tube guide groove 17c in which the fingers 40 to 46 press the tube 50, a tube regulation wall 17d formed by a recess extending along the tube guide groove 17c is formed in a direction in which the fingers 40 to 46 advance.

An elastic member 60 is provided in the recess. That is, the elastic member 60 is provided between the tube regulation wall 17d and tube 50. The elastic member 60 is provided in such a way as to act as a damper when the tube 50 is pressed and closed with a pressure higher than necessary by the fingers 40 to 46, preventing the tube 50 from deteriorating. The elastic member 60 has elasticity which withstands the pressure and closure of the tube. It is more preferable that the coefficient of friction of the elastic member 60 with the tube 50 is made low.

Also, an air vent filter 65 acting as a mutual communication member is provided in a portion in which are bonded the flow inlet 52 of the tube 50 and the reservoir 14. A lyophilic filter in which pores are formed is provided inside the air vent filter 65. The filter allows the liquid to pass therethrough, and blocks a passage of air bubbles.

In the embodiment, the air vent filter being made a member for connecting the reservoir 14 and the tube 50, it is possible to carry out a separation and insertion of the tube 50 with respect to the reservoir 14.

The pores formed in the filter are in a range of 0.1 μm to 1 μm, allowing the liquid to pass therethrough, and suppressing an intrusion into the tube 50 of air bubbles equal to or more than 0.1 μm or 1 μm generated in the reservoir 14.

Protrusions 17b are formed on side surfaces and rear surfaces in the proximal portion (on the fixing frame 13 side) of the first tube guide frame 17, and protrusions 17n are formed on side surfaces and rear surfaces at the leading extremity, while the same kinds of protrusion 18b and 18e are formed on outer front surfaces in the proximal portion, and at the leading extremity, of the second tube guide frame 18 too.

In a condition in which the first tube guide frame 17 and second tube guide frame 18 are bonded together, the protrusions 17b and 18b are made continuous ring shaped protrusions, and the protrusions 17n and 18e are made continuous ring shaped protrusions.

The tube unit 11 is slidingly inserted into the control unit 12. At this time, the protrusions 17b, 17n, 18b, and 18e are provided, thereby increasing a control unit 12 and tube unit 11 position accuracy, as well as reducing a resistance at a time of insertion or removal.

A protrusion 96 with a groove 96a is formed at the tail (on the fixing frame 13 side) of the tube unit 11. The protrusion 96 is used when pinching the groove 96a and removing the tube unit 11 from the control unit 12.

Continuing, a description will be given, referring to FIG. 5, of an operation relating to a transportation and discharge of the liquid according to the embodiment. In the condition shown in FIG. 5, the cam 20 is rotated (in a direction of an arrow R in the drawing) via the transmission mechanism by the torque from the step motor 70, and the finger 44 is pressed by the finger pressing surface 21d of the cam 20, pressing and closing the tube 50.

The finger 45 is also in abutment with a finger pressing surface 21d and finger pressing slope 22 bonding portion, pressing and closing the tube 50. Also, the finger 46 is on the finger pressing slope 22, and pressing the tube 50, but has a smaller amount of pressure than the finger 44, and is not completely pressing and closing the tube 50.

The fingers 41 to 43, being in the range of the arc portion 23 of the cam 20, are in an initial position in which they do not press. The finger 40 is in abutment with the finger pressing slope 22 of the cam 20 but, in this position, is not yet pressing and closing the tube 50.

On the cam 20 being further rotated in the direction of the arrow R from this position, the fingers 45 and 46 are pressed in this order by the finger pressing surface 21d of the cam 20, pressing and closing the tube 50. The finger 44 is released from the finger pressing surface 21d, opening the tube 50. The liquid flows into a position of a liquid flow portion 51 of the tube 50 in which the pressure and closure of the finger is released, or a position thereof in which the tube 50 is not yet pressed and closed.

On the cam 20 being further rotated by the step motor 70, the finger pressing slope 22 presses the fingers 40, 41, 42, and 43 in this order sequentially from the liquid inflow side to the outflow side, and each of the fingers, when reaching the finger pressing surface 21c, presses and closes the tube 50.

By repeating this kind of operation, the liquid is caused to flow from the flow inlet 52 side toward the flow outlet 53 side, and discharged from the flow outlet 53.

At this time, two of the fingers 40 to 46 abut against one of the finger pressing surfaces of the cam 20 and, when the finger pressing surface moves to a position in which it presses a next finger, it presses one of the fingers 40 to 46. The condition in which two fingers are pressed, and the condition in which one finger is pressed, are repeated in this way, thereby forming a condition in which at least one finger is always pressing and closing the tube 50. A structure of the micropump using this kind of motion of the fingers 40 to 46 is called a peristalitic drive method.

Consequently, according to the embodiment, as the tube unit 11 is separable from the control unit 12 including the cam 20 which presses the fingers 40 to 46 which press and close the tube 50, in a condition in which the tube unit 11 is alone, the tube 50 is maintained in an opened condition. For this reason, it is possible to prevent a decrease in discharge accuracy accompanying a deterioration in resilience due to a continuous pressure and closure of the tube 50, and maintain a desired discharge accuracy.

Also, it is conceivable that the resilience of the tube 50 deteriorates by repeating the pressure and closure, and opening, of the tube 50 for a long time, in which kind of case a tube replacement is needed, but it is possible to easily replace the tube 50 as the tube unit after a certain time of use.

Also, as the cam 20, step motor 70, and transmission mechanism are configured as the control unit 12, when the tube unit 11 is mounted in the control unit 12, it is not necessary that the kinds of pinion and gear in the previously described heretofore known technology are connected in mesh, meaning that there is no damage in a meshing process.

Also, in the event that the tube unit 11 is mounted in the control unit 12 in a direction parallel thereto, it is possible to place the fingers 40 to 46 into a condition in which they can press the tube. Consequently, no connection mechanism being needed between the motor module and pump module as in the heretofore known technology, it is possible to simplify the structure, it is possible to improve an assembling property, and furthermore, it is possible to realize a reduction in thickness.

Also, it is possible to make the tube unit 11 far lower in cost than the control unit 11 including the cam 20, step motor 70, transmission mechanism, and control circuit 30. Therein, in the event that the tube unit 11 including the tube 50 making direct contact with a chemical or the like is used once and thrown away, and the control unit 12 is repeatedly used, it is possible to reduce a running cost.

Also, the inner diameter and outer diameter of the tube 50 can be considered to have a variation in dimension. The variation in dimension thereof affects the discharge accuracy. Therein, by the tube 50 and the fingers 40 to 46 which have a length complying with the dimension of the tube 50 being made one set to form a tube unit, it is possible to improve the discharge accuracy.

Also, as the tube unit 11 is mounted inside the space 110 provided in the control unit 12, the first machine casing 15 and second machine casing 16 configuring the control unit 12 have a casing function, eliminating a need for a casing for housing the tube unit 11 and control unit 12, enabling the simplification in structure.

Also, as a structure is such that the tube unit 11 is inserted into the control unit 12 in a direction parallel thereto, it is possible to make the reduction in thickness in comparison with the kind of stacking structure in the heretofore known technology.

Also, the micropump 10 of the embodiment is configured so that the fingers 40 to 46 are pressed by the rotation of the cam 20, pressing and closing the tube 50. Consequently, it is necessary to cause the radius point P' of the arc shape of the tube 50 to coincide with the rotation center P of the cam.

Therein, when the tube unit 11 is mounted in the control unit 12, by providing guide portions (the wall surface 18a and wall surface 15a) one in each of them, and bringing the guide portions into abutment with each other, it is possible to cause the radius point P' of the arc shape of the tube 50 to approximately coincide with the rotation center P of the cam, and all of the fingers 40 to 46 can reliably carry out the pressure and closure of the tube without providing a dedicated position regulation member.

In the embodiment, one or all of the first machine casing 15, second machine casing 16, first tube guide frame 17, and second tube guide frame 18, or one portion or the whole of the first machine casing 15, second machine casing 16, first tube guide frame 17, and second tube guide frame 18, are formed of a transparent material.

By so doing, it is possible to observe the internal component parts or an engagement relationship and drive condition of each component part, and it is possible to detect whether the condition is normal, where there is a problem, or the like. It is sufficient that a range made transparent is at least a range of a portion desired to be observed.

Also, in the event of configuring in such a way that it is possible to observe from the direction of the upper portion, or the direction of the lower portion, of the reservoir 14, it is possible to observe the amount of liquid stored. It is more preferable to make the reservoir 14 a transparent container.

Also, by housing the reservoir 14 in the tube unit 11, it is possible to replace the tube 50 before deterioration in the event that the tube unit 11 including the tube 50 is replaced at a point at which the liquid in the reservoir 14 has run out, meaning that it is possible to increase the reliability of the micropump.

Also, a configuration is such that the air vent filter 65 is provided as a connection member between the reservoir 14 and tube 50, and the reservoir 14 and tube 50 are attachable to and detachable from one another. Consequently, by removing a reservoir 14 in which there is little chemical, and connecting a reservoir 14 in which is stored a chemical to the tube 50, it is possible to use the micropump for a long time.

Also, by providing the air vent filter 65 between the reservoir 14 and tube 50, it is possible to block a passage of air bubbles included in the liquid into the tube 50, and prevent the air bubbles from being injected into a living organism when discharging the liquid, which is a chemical, into the living organism, increasing safety.

Also, the reservoir 14 includes the septum 95 acting as a port for causing the liquid to flow thereinto, and sealing it therein. By providing the reservoir 14 with the septum 95, it is possible to easily carry out the injection of the liquid into the reservoir 14 in the condition in which the tube 50 is connected to the reservoir 14.

Furthermore, by disposing the septum 95 in such a way as to protrude outwardly of the first tube guide frame 17, and expose the flow inlet of the septum 95 to the outside of the fixing frame 13, it is possible to easily carry out the injection of the liquid into the reservoir 14 in the condition in which the tube unit 11 is alone, or in the condition in which the tube unit 11 is mounted in the control unit 12.

Furthermore, it is also possible to easily carry out an additional injection of the liquid in a condition in which the micropump 10 is in use.

Embodiment 2

Continuing, a description will be given, referring to the drawings, of Embodiment 2. Embodiment 2 has a feature in that there is provided an elastic member which biases the tube unit 11 toward the control unit 12. Consequently, a description will be given centered on differences from Embodiment 1.

FIGS. 8A and 8B showing one portion of a micropump according to Embodiment 2, FIG. 8A is a partial plan view, and FIG. 8B is a sectional view showing the E-E section of FIG. 8A. In FIG. 8A, a leaf spring 99 acting as the elastic member is provided between the tube unit 11 and fixing frame 13.

The leaf spring 99 is fixed to a concave, leaf spring fixing portion 13f provided on the tube unit 11 side of the fixing frame 13. The focal point of the leaf spring 99 is on a center line J, biasing the tube unit 11 toward the rotation center P of the cam 20.

By this means, the wall surface 18a of the tube unit 11 and the wall surface 15a of the control unit 12 are brought into abutment on the center line J.

The fixing of the leaf spring 99 is carried out using a fixing method such as thermally welding a guide shaft 13g protruded from the leaf spring fixing portion 13f of the fixing frame 13, as shown in FIG. 8B. As it is sufficient that the leaf spring 99 does not fall off in a condition in which the fixing frame 13 is fixed, the leaf spring 99 does not necessarily have to be fixed.

It is conceivable that, when the tube unit 11 is fixed to the control unit 12 using the fixing frame 13, a horizontal (plan direction) space occurs between the tube unit 11 and control unit 12 due to a variation in dimension of component parts such as the tube unit 11, control unit 12, fixing unit 13, and the like, and the tube 50 will not be able to be pressed and closed by the fingers 40 to 46.

Therein, by biasing the tube unit 11 in the direction of the control unit 12 by means of the leaf spring 99, it is possible to bring the wall surfaces 15a and 18a into abutment with each other, and cause the radius point P' of the arc shape of the tube 50 to coincide with the rotation center P of the cam 20, enabling all of the fingers 40 to 46 to reliably press and close the tube 50.

Also, the biasing force of the leaf spring 99 is set in such a way as to be greater than the pressure of the fingers 40 to 46 against the tube.

By so doing, when the fingers 40 to 46 press and close the tube 50, the tube unit 11 (that is, the tube 50) does not move in a direction away from the fingers 40 to 46, meaning that it is possible to reliably press and close the tube.

In the embodiment, the leaf spring 99 is exemplified as the elastic member but, not being limited to the leaf spring, it is acceptable to use a coil spring, or a flat plate having elasticity in a direction of thickness, and it is also acceptable to adopt a structure using a plurality thereof.

Embodiment 3

Continuing, a description will be given, referring to the drawings, of a micropump according to Embodiment 3. Embodiment 3 has a feature in that a power source is housed in the tube unit. Consequently, a description will be given centered on differences from Embodiment 1.

FIGS. 9A and 9B showing one portion of the micropump according to Embodiment 3, FIG. 9A is a partial plan view, and FIG. 9B is a sectional view showing the G-G section of FIG. 9A. In FIGS. 9A and 9B, a small button type battery 120 (hereafter expressed simply as a battery 120) acting as the power source is housed inside the tube unit 11.

The battery 120, together with the reservoir 14, is mounted in a recess formed in the first tube guide frame 17, and the top thereof is sealed by the second tube guide frame 18. Herein, when the lower surface, as seen in FIG. 9B, of the battery 120 is taken to be a minus pole, and the upper surface and side surface are taken to be a plus pole, the lower surface is connected to a minus terminal 121, and the side surface is connected to a plus terminal 122.

The minus terminal 121 and plus terminal 122 are connected by unshown leads to connection terminals 123 and 124 implanted upright at an extremity of the first tube guide frame 17.

The connection terminals 123 and 124 are protruded from the first tube guide frame 17, and extended as far as the interior of the control unit 12. Connection terminals (not shown) electrically independently connected to the connection terminals 123 and 124 are provided on the control unit 12, and these connection terminals are connected to the control circuit 30 (refer to FIG. 5).

In the condition in which the tube unit 11 is mounted in the control unit 12, electric power is supplied to the control circuit 30 from the battery 120, and the micropump 10 attains a drivable condition.

It is also acceptable to adopt a structure in which the battery 120 is housed inside the tube unit 11, and the reservoir 14 is provided outside the tube unit.

When changing a chemical in use, or when replacing a used tube 50, by replacing the battery 120 together with the tube 50 as the tube unit 11, it is possible to prevent a battery capacity from running short during use.

Also, the battery 120 is mountable in and removable from the tube unit 11. The configuration shown in FIGS. 9A and 9B shows one example in which the fixing screws 92 (refer to FIG. 5) which join the first tube guide frame 17 and second tube guide frame 18 together are removed, and the battery 120 mounted and removed.

Herein, as a battery 120 mounting and removing structure, it is acceptable to adopt a structure in which a battery cap is provided in the second tube guide frame 18, and it is also acceptable to adopt a structure in which, by establishing a structure in which the battery 120 is slidingly inserted from the tail (the fixing frame 13 side) of the tube unit 11, the battery 120 is mounted and removed with the fixing frame 13 removed.

In this embodiment, the small button type battery is exemplified as the battery, but it is possible to employ, apart from that, a secondary battery such as a sheet battery or a lithium ion battery. In the event of using these batteries, it is possible to dispose any one of them and the reservoir superimposed one on the other, and there is an advantage in that it is also possible to increase the capacity of the reservoir in the event of adopting a structure in which the battery is housed in the tube unit.

Embodiment 4

Continuing, a description will be given, referring to the drawings, of a micropump according to Embodiment 4. Embodiment 4 has a feature in that there is provided a detector, including a connection terminal and detection terminal, which detects whether the tube unit is inserted in an accurate position in the control unit. Consequently, a description will be given centered on differences from Embodiment 1.

FIGS. 10A and 10B showing one portion of the micropump according to Embodiment 4, FIG. 10A is a partial plan view, and FIG. 10B is a sectional view showing the H-H section of FIG. 10A. In FIGS. 10A and 10B, a first connection terminal 66 and second connection terminal 67 are implanted upright at peninsular extremities on both sides of the wall surface 18a formed in the tube unit 11.

One extremity of each of the first connection terminal 66 and second connection terminal 67 is electrically connected by a connection lead 94. Also, the other extremities are protruded from control unit side extremities 18c and 18d in such a way as to thrust into the interior of the control unit 12.

An approximately U-shaped spring shaped first detection terminal 68 and second detection terminal 69 are provided on the control unit 12 (the first machine casing 15). As the first detection terminal 68 and second detection terminal 69 are of the same shape, a description will be given exemplifying with the second detection terminal.

The second detection terminal 69 is mounted, bent, in a recess provided in the first machine casing 15. Herein, arms 69a and 69b of the second detection terminal 69 press opposed side walls in the recess.

Consequently, the arm 69a is positionally regulated by a side wall 15g in the recess. The position of the side wall 15g is accurately positionally regulated in relation to the position of the rotation center P of the cam 20. Also, the positions of the leading extremities of the first connection terminal 66 and second connection terminal 67 are also accurately positionally regulated in relation to the position of the rotation center P of the cam 20.

When the tube unit 11 is mounted in the control unit 12 as far as a position in which the arc shaped wall surface 18a of the tube unit 11 and the arc shaped wall surface 15a of the control unit come into abutment with each other, the second connection terminal 67 is electrically connected to the second detection terminal 69. At the same time, the first connection terminal 66 is also electrically connected to the first detection terminal 68.

A lead 64 is connected to the second detection terminal 69, and the lead 64 is connected to a detection terminal A (not shown) of the control circuit 30. Meanwhile, a lead 63 is connected to the first detection terminal 68, and the lead 63 is connected to a detection terminal B (not shown) of the control circuit 30.

Herein, when it is detected by the detection terminal A and detection terminal B that the second connection terminal 67 and second detection terminal 69, and the first connection terminal 66 and first detection terminal 68, have been electrically connected, it is determined that the wall surface 18a of the tube unit 11 and the wall surface 15a of the control unit have come into abutment with each other.

When in this kind of condition, it is determined that the radius point P' of the arc shape of the tube 50 coincides with the rotation center P of the cam 20, and the step motor 70 (not shown) is placed into a drivable condition by the control circuit 30.

Also, in the event that neither the second connection terminal 67 and second detection terminal 69, nor the first connection terminal 66 and first detection terminal 68, are electrically connected, it is determined that the tube unit 11 and control unit 12 are in a condition in which they are not mounted in a predetermined position, and a mounting of the tube unit 11 in the control unit 12 is done again.

In this embodiment, a contact type is exemplified as the detector, but it is possible to employ an optical detection or magnetic detection structure.

With this kind of configuration, by driving the step motor 70 in the event of detecting that the radius point P' of the arc shape of the tube 50 and the rotation center P of the cam 20 have been caused to coincide, it is possible to press and close, and open, the tube 50 as it is set, meaning that it is possible to transport the liquid at a desired flow per unit time.

Embodiment 5

Continuing, a description will be given, referring to the drawings, of a micropump according to Embodiment 5. Embodiment 5 has a feature in that a battery acting as the power source is housed in the control unit. Consequently, a description will be given centered on differences from Embodiment 1.

FIGS. 11A and 11B showing one portion of the micropump according to Embodiment 5, FIG. 11A is a plan view, and FIG. 11B is a sectional view showing the I-I section of FIG. 11A. In FIGS. 11A and 11B, a small button type battery 120 (hereafter expressed simply as a battery 120) acting as the power source is housed in the control unit 12.

The battery 120 is mounted in a recess formed in the first machine casing 15, and the top thereof is sealed and fixed by a battery cap 130. Herein, when the lower surface, as seen in FIG. 11B, of the battery 120 is taken to be a minus pole, and the upper surface and side surface are taken to be a plus pole, the lower surface is connected to a minus terminal 121, and the side surface is connected to a plus terminal 122.

The minus terminal 121 and plus terminal 122 are connected to power source terminals (not shown) of the control circuit 30 by unshown leads.

The battery cap 130 includes a battery guide portion 131 protruded in such a way as to surround the outer periphery of the battery 120, and a flange portion 134. Threads 132 are formed on the outer periphery of the battery guide portion 131, and engaged with a threaded portion of the second machine casing 16, thereby fixing the battery 120.

A groove 133 is formed in the battery cap 130, and an opening and closing of the battery cap 130 is carried out by inserting a coin or the like in the groove, and rotating the battery cap 130.

When screwing the battery cap 130, the junction of the flange portion 134 and second machine casing 16 is closely tightened. By using a packing as a seal material between the flange portion 134 and second machine casing 16, it is possible to further improve an airtightness.

As a battery cap 130 fixing structure, it is also acceptable to adopt a structure in which the battery cap 130 is pressed into the second machine casing 16. Also, it is also acceptable that the battery cap 130 is of a bayonet structure. It is also acceptable to adopt a structure in which an opening is provided in a side surface of the first machine casing 15 and second machine casing 16, and the battery 120 is inserted from the opening, and fixed by the same kind of fixing frame fixing structure as that of the fixing frame 13.

By housing the battery 120 in the control unit 12 in this way, it is possible to carry out a battery replacement in the condition in which the tube unit 11 is mounted in the control unit 12, or in a condition in which the control unit 12 is alone.

By housing the battery 120 in the control unit 12, it is possible to carry out a connection of the control circuit 30 and battery without using the kinds of connection terminal 123 and 124 in Embodiment 3 (refer to FIGS. 9A and 9B), enabling the simplification in structure.

Also, by disposing the battery 120 in a space of the control unit 12 outside a range in which the tube unit 11 is mounted, it is possible to make the battery 120 thicker than with the structure in which the battery 120 is mounted in the tube unit 11, meaning that it is possible to employ a battery with a larger capacity.

Furthermore, as a vacant space increases in the tube unit 11, it is possible to increase the liquid capacity of the reservoir 14 by that amount.

As heretofore described, with each previously described micropump 10 according to Embodiment 1 to Embodiment 5, the reduction in size and thickness is possible, enabling a minute amount of flow to flow stably and continuously, meaning that, mounted inside, or on the surface of, a living organism, it is suitable for a medical use such as a development of new drugs, a drug delivery, and the like. Also, in various kinds of mechanical apparatus, it is possible to mount the micropump 10 inside or outside the apparatus, and utilize it for transporting a fluid such as water, a salt solution, a chemical, an oil, an aromatic solution, ink, a gas, or the like. Furthermore, it is possible to utilize the micropump alone for causing the liquid to flow, and supplying the liquid.

The entire disclosure of Japanese Patent Application No. 2008-249798, filed Sep. 29, 2008 is expressly incorporated by reference herein.

What is claimed is:
1. A micropump comprising:
    a tube unit including a tube and a plurality of fingers;
    a control unit including a cam and a control circuit, the tube unit being attachable to and detachable from the control unit;
    wherein the tube unit has a power source which supplies power to the control circuit, and the tube deforms via the plurality of fingers in accordance with the rotation of the cam driven by the control circuit; and
    wherein a plurality of convexities are formed on the cam that form a plurality of finger pressing surfaces that actuate the plurality of fingers;
    the convexities each being separated by a planar surface that extends radially outward from a concentric surface formed on a circle of the cam, and each convexity including a finger pressing surface that includes a finger pressing slope surface and a surface that is arc-shaped, the surface that is arc-shaped being part of the concentric surface and provided in a position that does not press the fingers.
2. The micropump according to claim 1,
    wherein the power source is removably mounted to the tube unit.

3. The micropump according to claim 1, further comprising:
a reservoir detachably attached to the tube unit.

4. The micropump according to claim 3,
wherein the reservoir includes a re-sealable port for introducing fluid into the reservoir.

5. The micropump according to claim 1, further comprising:
a reservoir housed in the tube unit.

6. The micropump according to claim 1, further comprising:
a reservoir; wherein
the reservoir and the power source are housed in the tube unit.

7. A micropump comprising:
a tube unit including a tube and a plurality of fingers;
a control unit including a cam and a control circuit, the tube unit being attachable to and detachable from the control unit;
wherein the tube unit has a power source removably mounted directly thereto which supplies power to the control circuit; and
wherein a plurality of convexities are formed on the cam that form a plurality of finger pressing surfaces that actuate the plurality of fingers;
the convexities are each separated by a planar surface that extends radially outward from a concentric surface formed on a circle of the cam; and
each finger pressing surface includes a finger pressing slope surface and a surface that is arc-shaped, the surface that is arc-shaped being part of the concentric surface and provided in a position that does not press the fingers.

8. The micropump according to claim 7, further comprising
a reservoir detachably attached to the tube unit.

9. The micropump according to claim 8,
wherein the reservoir includes a re-sealable port for injecting a fluid thereinto.

10. The micropump according to claim 7, further comprising a reservoir housed in the tube unit.

* * * * *